United States Patent [19]

Franz

[11] 4,199,345
[45] Apr. 22, 1980

[54] DERIVATIVES OF N-TRIFLUOROACETYL-N-PHOSPHONOMETHYLGLYCINE DICHLORIDE

[75] Inventor: John E. Franz, Crestwood, Mo.

[73] Assignee: Monsanto Company, St. Louis, Mo.

[21] Appl. No.: 954,276

[22] Filed: Oct. 25, 1978

Related U.S. Application Data

[63] Continuation-in-part of Ser. No. 894,070, Apr. 6, 1978, abandoned.

[51] Int. Cl.$^2$ .................. A01N 9/36; C07C 101/06
[52] U.S. Cl. .................. 71/86; 260/544 Y; 560/172
[58] Field of Search .................. 71/86; 560/172; 260/544 Y

[56] References Cited

U.S. PATENT DOCUMENTS

| | | | |
|---|---|---|---|
| 3,278,652 | 10/1966 | Barnas et al. | 560/172 |
| 3,280,226 | 10/1966 | Barnas et al. | 260/544 Y |
| 3,799,758 | 3/1974 | Franz | 71/86 |
| 3,853,530 | 12/1974 | Franz | 71/86 |
| 3,970,695 | 7/1976 | Franz | 71/86 |

*Primary Examiner*—Catherine L. Mills
*Attorney, Agent, or Firm*—William T. Black; Donald W. Peterson

[57] ABSTRACT

This disclosure relates to N-trifluoroacetyl-N-phosphonomethylglycine dichloride derivatives and to herbicidal compositions containing same. The N-trifluoroacetyl-N-phosphonomethylglycine dichlorides are useful as post-emergent herbicides.

15 Claims, No Drawings

DERIVATIVES OF N-TRIFLUOROACETYL-N-PHOSPHONOMETHYLGLYCINE DICHLORIDE

This application is a continuation-in-part of application Ser. No. 894,070, filed Apr. 6, 1978, now abandoned.

This invention relates to N-trifluoroacetyl-N-phosphonomethylglycine dichloride derivatives, to herbicidal compositions containing same and to herbicidal methods. More particularly, this invention relates to N-trifluoroacetyl-N-phosphonomethylglycine trichlorides and to the monoesters of such compound.

In accordance with U.S. Pat. No. 3,970,695, issued July 20, 1976, N-perfluoroacyl-N-phosphonomethylglycines of the formula

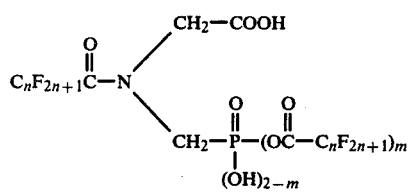

wherein n is an integer of from 1 to 4 and m is 1 or 0 are produced by reacting a perfluoroacyl anhydride with N-phosphonomethylglycine in the presence of a perfluoroalkanoic acid to form the compound of the formula wherein m is 1 and then by hydrolysis to form the compounds wherein m is 0.

N-phosphonomethylglycine, its salts, amides, esters and other derivatives are disclosed in U.S. Pat. No. 3,799,758 and are shown to be post-emergent herbicides. Other derivatives of N-phosphonomethylglycine and the plant growth regulation use thereof are disclosed in U.S. Pat. No. 3,853,530.

The N-trifluoroacetyl-N-phosphonomethylglycine dichloride derivatives of this invention are those having the formula

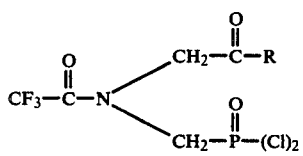

wherein R is chlorine, an alkoxy group containing from 1 to 10 carbon atoms, an alkoxyalkoxy group containing from 3 to 6 carbon atoms, an alkoxyalkoxyalkoxy group containing from 5 to 9 carbon atoms or a chloro lower alkoxy group.

As employed herein, "chloro lower alkoxy" designates those alkoxy groups containing up through four carbon atoms in a straight or branched chains and up to three chlorine groups.

Illustrative of the alkoxyalkoxy groups which R represents are methoxyethxoy, methoxypropoxy, methoxybutoxy, ethoxyethoxy, ethoxypropoxy, propoxyethoxy, propoxypropoxy and the like. Illustrative of the alkoxyalkoxyalkoxy groups represented by R are, for example, methoxyethoxyethoxy, methoxyethoxypropoxy, methoxypropoxypropoxy, methoxypropoxybutoxy, ethoxyethoxyethoxy, propoxypropoxypropoxy and the like.

The compounds of this invention are prepared by reacting an N-phosphonomethylglycine of the formula

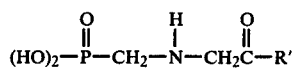

or ester thereof wherein R' is hydroxy or an R group as hereinabove defined except that R' cannot be chlorine with trifluoroacetic acid anhydride at temperatures from about 10° C. to about 35° C. and then treating the reaction product with excess thionyl chloride under refluxing conditions. For best yields, the intermediate reaction product is preferably stripped of the excess trifluoroacetic anhydride prior to the addition of the thionyl chloride. The excess thionyl chloride is removed after the reaction is completed to yield the compounds of this invention.

The compounds of this invention are useful as herbicides.

The following non-limiting examples will serve to further demonstrate to those skilled in the art the manner in which specific compounds within the scope of this invention can be prepared and also their use as herbicides.

EXAMPLE 1

To 100 ml. trifluoroacetic anhydride (145 g, 0.69 mole) was added 60 g (0.3 mole) of ethyl N-phosphonomethylglycinate portionwise over 1.5 hours. The reaction mixture was stirred for an additional 2 hours after which a completely homogeneous solution was obtained. The solution was concentrated in vacuo first at 20 mm. then at 0.5 mm Hg. The residue (112 g) was treated with 172 g (1.45 mole) of thionyl chloride and the resulting mixture was refluxed for 2 hours. The mixture was concentrated in vacuo and triturated with hexane to afford ethyl N-trifluoroacetyl-N-dichlorophosphonomethylglycinate as white needles, 96 g (96%), m.p. 77.5°–79.5° C.

Anal. Calc'd: C, 18.74; H, 1.26; N, 4.37. Found: C, 18.94; H, 1.42; N, 4.37.

EXAMPLE 2

To a mixture of 5.1 g (0.03 mole) N-(phosphonomethyl)glycine and 10 ml. trifluoroacetic acid was added 19 g (13 ml, 0.09 mole) trifluoroacetic anhydride. The solution was stirred overnight at room temperature and then concentrated in vacuo to an amorphous yellow solid (9.0 g). This material was dissolved in 25 ml. thionyl chloride and refluxed gently for 1.5 hours. The excess thionyl chloride was removed by distillation and the residual waxy solid was extracted with hot hexane. A solid product separated on cooling and was isolated by filtration and identified as N-trifluoroacetyl-N-(dichlorophosphonomethyl)glycinyl chloride in a yield of 8.3 g (92%), m.p. 78°–81° C.

Anal. Calc'd: C, 18.74; H, 1.26; N, 4.37. Found: C, 18.94; H, 1.42; N, 4.37.

EXAMPLE 3

To 100 ml. (145 g, 0.69 mole) of trifluoroacetic anhydride was added slowly 68.9 g (0.306 mole) butyl N-(phosphonomethyl)glycinate. After 2 hours, the solution was concentrated in vacuo. The residue was refluxed with 125 ml. thionyl chloride for 4 hours and excess thionyl chloride was then removed by distillation to yield butyl N-trifluoroacetyl-N-(dichlorophosphonomethyl)glycinate (88.9 g), m.p. 56°–58° C.

Anal. Calc'd: C, 30.19; H, 3.66; N, 3.91; P, 8.69. Found: C, 30.19; H, 3.74; N, 3.94; P, 8.95.

EXAMPLE 4

To 100 ml. (145 g, 0.69 mole) of trifluoroacetic anhydride was added slowly 66.5 g 2-methoxyethyl N-(phosphonomethyl)glycinate. After two hours, the reaction mixture was concentrated in vacuo and the residue was refluxed with 75 ml. thionyl chloride for 3 hours. Excess thionyl chloride was removed by distillation in vacuo. The residual oil was recrystallized from hexane to afford 101.1 g of 2-methoxyethyl N-trifluoroacetyl-N-(dichlorophosphonomethyl)-glycinate having a m.p. 51°–53.3° C.

Anal. Calc'd: C, 26.69; H, 3.08; N, 3.89; P, 8.60. Found: C, 27.04; H, 3.21; N, 3.95; P, 8.81.

EXAMPLE 5

To 40 ml. (58 g, 0.28 mole) trifluoroacetic anhydride was added 32.85 g (0.14 mole) 2-chloroethyl N-(phosphonomethyl)glycinate. The reaction was stirred overnight at 20° C., then concentrated in vacuo to a residual oil. This oil was treated with 70 ml. thionyl chloride at reflux for 2 hours, then concentrated in vacuo to yield 2-chloroethyl N-trifluoroacetyl-N-(dichlorophosphonomethyl)-glycinate as a white solid (47.6 g), m.p. 74°–77° C.

Anal. Calc'd: C, 23.07; H, 2.21; N, 3.84; P, 8.50. Found: C, 23.37; H, 2.41; N, 4.04; P, 8.54.

EXAMPLE 6

To 28 ml. (0.19 mole) trifluoroacetic anhydride was added 26 g (0.084 mole) n-Decyl N-(phosphonomethyl)glycinate and the solution was stirred for 24 hours. The mixture was concentrated in vacuo and the residue was refluxed with 53.5 g thionyl chloride for three hours. The excess thionyl chloride was removed by distillation to afford 34.8 g of n-Decyl N-trifluoroacetyl-N-(dichlorophosphonomethyl)glycinate as a white solid, m.p. 53.5°–55° C.

Anal. Calc'd: C, 40.74; H, 5.70; N, 3.17. Found: C, 41.15; H, 5.90; N, 3.21.

EXAMPLE 7

The post-emergence herbicidal activity of the various compounds of this invention is demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/cm$^2$ absolute. The atomizer contains 6 ml. of a solution or suspension of the chemical and an amount of a cyclohexanone emulsifying agent mixture so that the spray solution or suspension contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the four-week observations are omitted.

The post-emergence herbicidal activity index used in Table I is as follows:

| Plant Response | Index |
|---|---|
| 0–24% control | 0 |
| 25–49% control | 1 |
| 50–74% control | 2 |
| 75–99% control | 3 |
| 100% control | 4 |

The plant species utilized in these tests are identified by letter in accordance with the following legend:

| | |
|---|---|
| A - Canada Thistle* | K - Barnyardgrass |
| B - Cocklebur | L - Soybean |
| C - Velvetleaf | M - Sugar Beet |
| D - Morningglory | N - Wheat |
| E - Lambsquarters | O - Rice |
| F - Smartweed | P - Sorghum |
| G - Yellow Nutsedge* | Q - Wild Buckwheat |
| H - Quackgrass* | R - Hemp Sesbania |
| I - Johnsongrass* | S - Panicum Spp |
| J - Downy Brome | T - Crabgrass |

*Established from vegetative propagules.

Table I

| Compound of Example No. | WAT | kg/h | A | B | C | D | E | F | G | H | I | J | K |
|---|---|---|---|---|---|---|---|---|---|---|---|---|---|
| 1* | 4 | 11.2 | 4 | 4 | 4 | 4 | 4 | 4 | 2 | 3 | 3 | 3 | 4 |
| 1** | 4 | 4.8 | 1 | 2 | 4 | 2 | 2 | 1 | 1 | 1 | 1 | 0 | 2 |
| 1** | 4 | 11.2 | 2 | 3 | 4 | 2 | 4 | 0 | 1 | 1 | 1 | 1 | 3 |
| 2* | 4 | 11.2 | 2 | 3 | 4 | 3 | 4 | 2 | 1 | 3 | 2 | 4 | 3 |
| 2** | 4 | 11.2 | 0 | 1 | 1 | 1 | 1 | 1 | 0 | 0 | 0 | 0 | 0 |
| 3 | 4 | 11.2 | 1 | 3 | 3 | 2 | 2 | 2 | 2 | 3 | 3 | 2 | 3 |
| 3 | 4 | 5.6 | 1 | 2 | 1 | 2 | 4 | 1 | 2 | 4 | 3 | 2 | 3 |
| 4 | 4 | 11.2 | 3 | 4 | 4 | 3 | 4 | 4 | 3 | 4 | 3 | 4 | 4 |
| 4 | 4 | 5.6 | 1 | 2 | 0 | 2 | 4 | 3 | 3 | 3 | 2 | 0 | 3 |
| 5 | 4 | 11.2 | 3 | 3 | 4 | 3 | 3 | 4 | 3 | 2 | 3 | 2 | 3 |
| 5 | 4 | 5.6 | 2 | 3 | 2 | 1 | 0 | 2 | 2 | 0 | 2 | 1 | 3 |

Table I-continued

| Compound of Example No. | WAT | kg/h | A | B | C | D | E | F | G | H | I | J | K |
|---|---|---|---|---|---|---|---|---|---|---|---|---|---|
| 6*** | 2 | 11.2 | 0 | 0 | 0 | 0 | 0 | 0 | 0 | 0 | 0 | 0 | 0 |

*Dissolved, formulated and sprayed within 2 minutes.
**Sprayed in anhydrous acetone at 935 liters/hectare.
***Sprayed in anhydrous tetrahydrofuran at 935 liters/hectare.

Table II

| Compound of Example No. | WAT | Kg/h | L | M | N | O | P | B | Q | D | R | E | F | C | J | S | K | T |
|---|---|---|---|---|---|---|---|---|---|---|---|---|---|---|---|---|---|---|
| 1** | 4 | 4.8 | 2 | 3 | 1 | 1 | 1 | 4 | 2 | 3 | 2 | 4 | 2 | 3 | 2 | 4 | 3 | 3 |
| 1 | 2 | 4.8 | 2 | 1 | 2 | 0 | 1 | 3 | 1 | 2 | 2 | 2 | 2 | 2 | 1 | 3 | 2 | 3 |
| 2 | 2 | 4.8 | 1 | 1 | 1 | 1 | 1 | 1 | 1 | 1 | 0 | 1 | 1 | 1 | 1 | 1 | 0 | 2 |
| 2** | 4 | 4.8 | 1 | 1 | 0 | 0 | 1 | 1 | 0 | 1 | 0 | 0 | 0 | 1 | 0 | 0 | 0 | 2 |
| 3 | 4 | 5.6 | 2 | 4 | 4 | 1 | 4 | 4 | 3 | 3 | 4 | 4 | 4 | 3 | 4 | 4 | 4 | 4 |
| 3 | 4 | 1.12 | 1 | 4 | 1 | 0 | 1 | 2 | 1 | 2 | 3 | 4 | 4 | 1 | 2 | 4 | 3 | 4 |
| 4 | 4 | 5.6 | 3 | 4 | 4 | 3 | 4 | 4 | 4 | 4 | 4 | 4 | 4 | 3 | 4 | 4 | 4 | 4 |
| 4 | 4 | 1.12 | 1 | 2 | 1 | 1 | 3 | 2 | 2 | 2 | 1 | 2 | 3 | 1 | 3 | 4 | 3 | 3 |
| 5 | 4 | 5.6 | 3 | 4 | 4 | 4 | 4 | 3 | 3 | 4 | 4 | 4 | 4 | 4 | 4 | 4 | 4 | 4 |
| 5 | 4 | 1.12 | 1 | 2 | 1 | 1 | 3 | 3 | 2 | 2 | 1 | 4 | 3 | 2 | 2 | 4 | 4 | 4 |
| 6*** | 4 | 5.6 | 1 | 0 | 0 | 0 | 0 | 0 | 0 | 1 | 0 | 2 | 2 | 0 | 0 | 2 | 0 | 3 |

**Sprayed in anhydrous acetone at 935 liters/hectare.
***Sprayed in anhydrous tetrahydrofuran at 1870 liters/hectare.

From the test results presented in Tables I and II, it can be seen that the post-emergent herbicidal activity of the compounds of this invention is, for the most part, general in nature. In certain specific instances, however, some selectivity is demonstrated. In this regard it should be recognized that each individual species selected for the above tests is a representative member of a recognized family of plant species.

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Where required, from about 0.1 to 2.0 parts by weight of the inert liquid extender can be replaced by a corrosion inhibitor or anti-foaming agent, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid or organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent", it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

The application of an effective amount of the compounds of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.112 to about 22.4 or more kilograms per hectare. In pre-emergent treatments, the rate of application can be from about 0.56 to about 22.4 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound of the formula

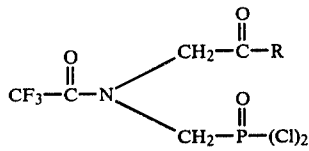

wherein R is chlorine, an alkoxy group containing from 1 to 10 carbon atoms, an alkoxyalkoxy group containing from 3 to 6 carbon atoms, an alkoxyalkoxyalkoxy group containing from 5 to 9 carbon atoms or a chloro lower alkoxy group.

2. A compound of claim 1 wherein R is ethoxy.
3. A compound of claim 1 wherein R is butoxy.
4. A compound of claim 1 wherein R is methoxyethyloxy.
5. A compound of claim 1 wherein R is chloroethoxy.
6. A herbicidal composition comprising an inert adjuvant and a herbicidally effective amount of a compound of claim 1.
7. A herbicidal composition comprising an inert adjuvant and a herbicidally effective amount of a compound of claim 2.
8. A herbicidal composition comprising an inert adjuvant and a herbicidally effective amount of a compound of claim 3.
9. A herbicidal composition comprising an inert adjuvant and a herbicidally effective amount of a compound of claim 4.
10. A herbicidal composition comprising an inert adjuvant and a herbicidally effective amount of a compound of claim 5.
11. A herbicidal method which comprises applying to a plant a herbicidally effective amount of a compound of claim 1.
12. A herbicidal method which comprises applying to a plant a herbicidally effective amount of a compound of claim 2.
13. A herbicidal method which comprises applying to a plant a herbicidally effective amount of a compound of claim 3.
14. A herbicidal method which comprises applying to a plant a herbicidally effective amount of a compound of claim 4.
15. A herbicidal method which comprises applying to a plant a herbicidally effective amount of a compound of claim 5.

* * * * *